United States Patent
Schmidt et al.

(10) Patent No.: US 8,059,264 B2
(45) Date of Patent: Nov. 15, 2011

(54) MONITORING VELOCITIES IN A POLYMERIZATION PROCESS

(75) Inventors: Christian Ulrich Schmidt, Bonn (DE); Stefan Ziegler, Eusserthal (DE); Gabriele Mei, Ferrara (IT); Stefano Bertolini, Bassano del Grappa-Vicenza (IT); Gerben Meier, Frankfurt (DE)

(73) Assignee: Basell Poliolefine Italia, s.r.l., Milan (IT)

( * ) Notice: Subject to any disclaimer, the term of this patent is extended or adjusted under 35 U.S.C. 154(b) by 727 days.

(21) Appl. No.: 10/547,659

(22) PCT Filed: Feb. 24, 2004

(86) PCT No.: PCT/EP2004/001845
§ 371 (c)(1), (2), (4) Date: Nov. 13, 2006

(87) PCT Pub. No.: WO2004/078792
PCT Pub. Date: Sep. 16, 2004

(65) Prior Publication Data
US 2007/0159628 A1     Jul. 12, 2007

Related U.S. Application Data

(60) Provisional application No. 60/454,483, filed on Mar. 13, 2003.

(30) Foreign Application Priority Data

Mar. 5, 2003    (EP) .................................... 03075652

(51) Int. Cl.
*G01N 21/85*    (2006.01)
*G01P 5/00*    (2006.01)

(52) U.S. Cl. ............... 356/27; 356/28; 436/69; 436/94; 702/26

(58) Field of Classification Search ............ 356/27, 356/28
See application file for complete search history.

(56) References Cited

U.S. PATENT DOCUMENTS

| 3,393,255 | A | * | 7/1968 | Pell et al. ..................... 264/3.1 |
| 4,752,131 | A |   | 6/1988 | Eisenlauer et al. .......... 356/338 |
| 4,963,498 | A | * | 10/1990 | Hillman et al. ................ 436/69 |

(Continued)

FOREIGN PATENT DOCUMENTS
DE    3833899    4/1989

(Continued)

OTHER PUBLICATIONS

Z. Q. Mao et al., "Particle Image Velocimetry: Direct Pulsed Image Recording on a Bistable Optically Addressed Spatial Light Modulator for Real-Time Fluid Flow Mapping," *Optics Letters, Optical Society of America*, Washington, US, vol. 20(2), p. 207-209 (Jan. 15, 1995) XP000486647.
R. H. Perry & D. W. Perry, *Perry's Chemical Engineers' Handbook*, $6^{th}$ Edition, McGraw Hill, p. 5-47 (1984).

*Primary Examiner* — Gregory J Toatley
*Assistant Examiner* — Rebecca C Slomski
(74) *Attorney, Agent, or Firm* — Dilworth IP, LLC

(57) ABSTRACT

Method for monitoring the velocity of growing polymer particles flowing in a two-phase stream during a polymerization process, said method comprising measuring the degree of attenuation in the propagation of light in said two-phase stream by means of a photometric instrument, said photometric instrument comprising: one or more transmitting optical waveguides connecting one or more light sources to said two-phase stream, one or more receiving optical waveguides connecting said two-phase stream to a light detector.

19 Claims, 3 Drawing Sheets

U.S. PATENT DOCUMENTS

| | | | |
|---|---|---|---|
| 5,864,392 A * | 1/1999 | Winklhofer et al. | 356/28 |
| 7,127,356 B2 * | 10/2006 | Nicoli et al. | 702/26 |
| 2002/0081744 A1 * | 6/2002 | Chan et al. | 436/94 |
| 2002/0093641 A1 * | 7/2002 | Ortyn et al. | 356/28 |

FOREIGN PATENT DOCUMENTS

| | | |
|---|---|---|
| EP | 0472899 | 3/1992 |
| EP | 0782587 | 7/1997 |
| EP | 1012195 | 6/2000 |

\* cited by examiner

MONITORING VELOCITIES IN A POLYMERIZATION PROCESS

This application is the U.S. national phase of International Application PCT/EP2004/001845, filed Feb. 24, 2004, claiming priority to European Patent Application 03075652.2 filed Mar. 5, 2003, and the benefit under 35 U.S.C. 119(e) of U.S. Provisional Application No. 60/454,483, filed Mar. 13, 2003; the disclosures of International Application PCT/EP2004/001845, European Patent Application 03075652.2 and U.S. Provisional Application No. 60/454,483, each as filed, are incorporated herein by reference.

The present invention relates to a method for running a polymerization process safely and in a reproducible way by monitoring the flow of polymer particles during the process. More specifically, the present invention relates to a method for monitoring the velocity of polymer particles in a process for the polymerization of olefins by means of a photometric instrument.

It is known that the measurement of the velocity of solid particles flowing in a liquid or gaseous medium is of great importance in many industrial processes, such as, for instance, the production of chemicals and the polymerization processes.

Liquid-solid mixtures or gas-solid mixtures are characterized by discontinuity in several properties, such as density, electrical conductivity and incident light behavior. By exploiting the differences in the above properties, many devices have been developed in order to measure the flow rate of solid particles entrained by a gaseous or liquid stream.

In particular cases, for example for vertical pipes, it is possible to estimate said velocity by measuring the differential pressure between two sections of the pipe in order to determine the total density of a two-phase mixture comprising solid and gas. Starting from the value of gas flow rate measured by a common gas flowmeter, it is possible to obtain the relative velocity of the solid particles with respect to the gas velocity by means of particular empirical formulas (see Perry, R. H., and Green, D. W.: *Perry's Chemical Engineers' Hand-book*, 6th ed., McGraw Hill, 1984, pag. 5-47). It goes without saying that uncertainty is related to the use of said empirical formulas and, in particular, uncertainty rises with the increase of solid concentration.

Another system, provided by Auburn International Inc., measures the small amount of charge generated due to frictional electrification, known as triboelectric effect when a non-conductive liquid or solid flows in a pipe. These charges, which are formed during frictional contact between dissimilar materials, are what normally lead to electrostatic build up if they are not allowed to dissipate, i.e. if the pipe is not grounded. The device consists of a sensor pipe made of an insulating material which is inserted in line and matches the existing inner diameter of the line. Two sensitive ring electrodes are placed around the outside of the sensor pipe at some set distance apart. As the charges accumulated in the liquid or solid pass through the electrodes, a small but measurable current is induced due to capacitive coupling. This induced current is amplified and digitized as a waveform from each sensor. If the ring electrodes are not too far apart, the distribution of triboelectric charge in the flowing stream does not change significantly as it flows from the first to the second electrode. Thus, the measured waveforms at each sensor are similar in shape but shifted in time due to the time required to pass from the first to the second electrode. The solid velocity is obtained by dividing the known ring sensor separation distance by the measured time delay. Unfortunately, this system can fit only small-diameter pipes, therefore is completely useless for large-diameter pipes or reactors.

Apart from the physical principles exploited by different instruments, most of the systems available on commerce involve sampling through lateral apertures in the wall of the pipes. The interaction between the mechanical parts of the sensors and the product to be sampled can cause unacceptable disturbance in the flow conditions.

Moreover, when the solid particles belong to a reacting system, as in the polymerization processes, it is important to avoid any alteration of the reaction conditions. For the above reasoning, invasive devices are not suitable to carry out the velocity measurements when they interfere with the polymerization conditions.

Other methods known in the art are not suitable to be used in polymerization processes. For example, the addition of radioactive particles to the flow of polymer in order to measure the circulation of solid in the system is not feasible since the radioactive particles would be inevitably removed together with the discharged polymer. Moreover, the presence of radioactive particles in the reaction medium would interfere with the measurements carried out by γ-ray instruments, that are commonly used in polymerization processes in order to provide density measurements.

Also optical systems based on the interaction between electromagnetic waves and the solid, including fiber-optical ones, are already available for use in some industrial processes. Photometric instruments based on the degree of attenuation in the light propagation in dispersed system have been described.

DE-A-38 33 899, for example, discloses a spectrophotometer for remote measurement in which optical waveguides between a measurement-light unit and a unit for processing residual light are connected to samples by means of windows, and an actuatable filter wheel is arranged between a flash lamp serving as the measurement-light source and a beam splitter. This is an improvement over customary photometers in that the accuracy of the measurement of the reference and measurement signals is improved by pulsing. However the use of a pulsed system is disadvantageous when a continuous process control is required. Moreover, this photometer cannot be used in highly concentrated systems.

Also the laser-optical arrangement described in U.S. Pat. No. 4,752,131 having a similar structure for analyzing individual particles of dispersions and suspensions in order to determine the degree of dispersion shows the same disadvantages of the previous one.

The prior art methods and devices fail in providing high-precision velocity measurements when applied to the large-diameter pipes and/or reactors at the challenging conditions of pressure and temperature involved in a polymerization process.

In EP 472899 a photometric instrument for measuring the degree of attenuation in the propagation of light in disperse systems has been disclosed. Said photometric instrument is suggested to be used for determining the colour of suspensions or the size of solid particles distributed therein or the concentration of the solid. The use of said instrument for measuring the velocity of solid particles flowing in a gaseous or liquid medium is not disclosed in EP 472899.

It would be desirable to provide a non-invasive measuring instrument capable of working at severe conditions of pressure and temperature providing efficient and accurate measurements of polymer particles velocity in a polymerization process.

It has now unexpectedly been found that when operating in a polymerization process wherein high temperature and pressure are required, very accurate velocity measurements of solid particles can be continuously obtained by the use of a particular photometric instrument.

It is therefore an object of the present invention a method for monitoring the velocity of growing polymer particles flowing in a two-phase stream during a polymerization process, said method comprising measuring the degree of attenuation in the propagation of light in said two-phase stream by means of a photometric instrument, said photometric instrument comprising:

one or more transmitting optical waveguides connecting one or more light sources to said two-phase stream, one or more receiving optical waveguides connecting said two-phase stream to a light detector.

The method according to the present invention is suitable for monitoring the velocity of solid particles flowing in a two-phase stream, so that it can be advantageously applied in the control of the solid circulation during a polymerization process.

In a polymerization process the catalyst particles and the monomers are fed together into the reaction zone in the presence of a reaction medium. In most processes, as the polymerization proceeds, a two-phase stream containing polymer particles is formed. Depending on whether the polymerization is carried out in gas or liquid phase, said two-phase stream can be a gas/solid stream or a liquid/solid stream, and comprises the solid polymer particles growing in contact with one or more monomers.

The method of the present invention is preferably applied to any polymerization process wherein a polymer concentration in said two-phase stream is comprised between 5 and 70% by volume and wherein the flow of polymer particles is substantially along one direction. For instance, a gas- or liquid-phase polymerization carried out in a loop reactor or in a tubular reactor are within the scope of the invention.

The control method of the invention exploits the photometric instrument described in EP 472 899 applied to the measurement of the velocity of polymer particles flowing within pipes or reactors.

The working of said photometric instrument is based on the determination of the intensity of light reaching a detector from a light source as a function of the properties of polymer particles flowing in a gas or liquid medium. Depending on the arrangement of the light source, the light detector and the two-phase stream, there are various dependencies of the measured signal on the stream properties. The reason for this is that the propagation or attenuation of light is a function of the fluidization conditions of the two-phase stream and, more in general, of its properties of scattering and absorption. The optical properties of the two-phase stream allow conclusions to be drawn on the polymer flow, said polymer flow being at the basis of the process control.

The photometric instrument used in the present invention can work, as described in EP 472 899, according to three different types of measurement arrangements: transmission, quasi-backscattering and remission mode.

In transmission mode, the light transmitted through the two-phase stream is measured. In quasi-backscattering mode, the light scattered back in the direction of incidence as a consequence of diffuse propagation of light in the disperse medium but entering another fiber is measured.

In remission mode, the light reflected in a diffuse manner at the medium-side interface of a transparent flat element terminating the optical waveguide, but generally not the reflection of the interface itself, is measured.

It has been found that a quasi-backscattering arrangement of the optical waveguide connection reveals particularly advantageous to fulfill the aim of the present invention, that is an accurate and continuos control of the velocity of polymer particles during the polymerization.

The photometric instrument can be conveniently placed in any point of the polymerization reactor fitting it to the wall of the reactor. One or more transmitting optical waveguides and one or more receiving optical waveguides of the optical waveguide connection can be arranged in a quasi-backscattering arrangement on the wall of the reactor.

Accurate results in process control during the polymerization can be obtained by avoiding as much as possible any interference with the polymerization conditions. This is achieved by arranging the ends of the transmitting and receiving optical waveguides so as not to project sensibly into the interior of the reactor. Preferably, the reactor-side ends of the transmitting and receiving optical waveguides are positioned flush with respect to the wall of the reactor. The light coming from the light source reaches the two-phase stream containing polymer particles via the transmitting optical waveguides and is then scattered back by the polymer in the direction of incidence so entering the receiving optical waveguides.

As known in the art of the optical waveguide connection, each transmitting optical waveguide can contain one or more transmitter fibers and each receiving optical waveguide can contain one or more receiver fibers.

According to a preferred embodiment, the reactor-side ends of said transmitting and receiving optical waveguides are arranged alongside one another in pairs. A first and a second pair of transmitting and receiving optical waveguides are positioned at a suitable distance in the direction of the polymer flow. That it to say, in said embodiment the photometric instrument comprises two transmitting optical waveguides connecting the light source to the wall of the reactor and two receiving optical waveguides connecting the wall of the reactor to a light detector. The reactor-side ends of the two transmitting optical waveguides, as well as the reactor-side ends of the two receiving optical waveguides are placed at a distance of less than 10 mm, preferably at a distance of 0.2 to 6 mm, along the flow of the polymer particles.

In gas-phase polymerization processes, it can be advantageous to arrange a fluxing of monomer(s), inert gas(es) or a mixture thereof that, working on-demand, is able to clean the ends of the optical waveguides, blowing away fines, chunks and sheets deposited thereon. Said fluxing is arranged close to the ends of the optical waveguides, preferably tangential to said ends.

When used for monitoring the velocity of polymer particles running inside a polymerization reactor, the method of the present invention provides a high precision evaluation of the polymer velocity even if the polymerization is carried out in severe conditions of temperature, pressure and polymer concentration. Even with polymer concentration in the range of from 30 to 70% by volume, the method of invention can give excellent and reproducible results.

Severe polymerization conditions occur, for instance, in the gas phase process disclosed in EP 0 782 587 and EP 1 012 195, wherein the polymerization is carried out in two interconnected polymerization zones. The method of the present invention will be now illustrated, but not being limited to, with reference to the polymerization of one or more α-olefins carried out in said gas-phase process, in which the growing polymer particles flow upward through a first polymerization zone under fast fluidization conditions, leave said first polymerization zone and enter a second polymerization zones through which they flow in a densified form under the action of gravity, leave said second polymerization zone and are reintroduced into said first polymerization zone, thus establishing a circulation of polymer between the two polymerization zones.

The operating conditions in said second polymerization zone are particularly severe for traditional velocity measurement instruments: the temperature is between 50° C. and 120° C.; the pressure is between 1.5 MPa and 6 MPa and the polymer concentration ($m^3$ of polymer per $m^3$ of reactor) is generally comprised between 30 and 60% by volume, said concentration being particularly high since the polymer flows in a densified form under the action of gravity.

Because of the high concentration of the solid particles, any relative motion between adjacent particles is virtually absent, so that a uniform downward flow of solid run through said second polymerization zone at a velocity generally comprised between 0.1 and 1 m/s.

Velocity measurements, in combination with density measurements, obtained for instance by means of a γ-rays instrument, provide a direct and highly-precise measurement of the mass flow rate of polymer, i.e. the circulation rate, which is a very important parameter in polymerization processes, particularly in the polymerization processes described in EP 0 782 587 and EP 1 012 195. The velocity of the polymer particles affects the mean number of times the polymer passes through the two different polymerization zones (cycles) above described. As a result, some properties, such as for example the homogeneity, the molecular weight distribution and the copolymer composition distribution of the obtained polymer can be controlled by adjusting the velocity of said polymer particles flowing within the reactor. The goal is that to keep said velocity under control, in order to obtain products with the desired quality.

The circulation rate is of particular importance when producing bimodal homopolymers or copolymers, i.e. when two polymerization zones at different composition are established within the reactor. As described in EP 1 012 195, it is possible to obtain, within the reactor, two polymerization zones at different compositions by feeding a gas or liquid mixture to the top of the second polymerization zone. Said mixture acts as a barrier to the gas coming from the first polymerization zone. Any fluctuations in the polymer circulation rate affect the efficiency of said barrier. In fact, the higher the circulation rate, the higher the gas coming from the first polymerization zone and, consequently, the higher the gas or liquid mixture flow rate to be fed to the top of the second polymerization zone.

Also in monomodal production, when no barrier is fed, the circulation rate is a critical parameter. In fact, the polymer velocity affects directly the temperature within the reactor. Polymerization is an exothermic process, so that heat removal is necessary to avoid hot spots inside the reactor. If hot spots are formed, melting of polymer can occur, with consequent formation of chunks and fouling of the walls, which can lead to shut-down the reactor. The temperature of the polymer increases as it descends in the second polymerization zone, so that in the bottom part thereof the situation is particularly critical. Due to the high concentration of polymer, relatively low heat transfer coefficient is assured and little amounts of gas act as cooling medium. For equal cooling, the lower the velocity of the polymer particles, the higher the temperature in the second polymerization zone. Therefore, it is important that the solid polymer particles reside in said zone only for the time required by the process. Accordingly, the photometric instrument is advantageously arranged in the second polymerization zone to keep under control the polymer velocity or, in other words, the loop circulation of solid inside the reactor. Preferably, the photometric instrument is arranged on the bottom part of said second polymerization zone.

The velocity of the solid polymer particles circulating between the two polymerization zones can be conveniently controlled by means of a restriction, for example being shaped like a funnel, placed at the bottom of the second polymerization zone, and an adjustable mechanical valve being positioned downstream the restriction. Advantageous examples of said mechanical valve are throttle valves and butterfly valves.

In order to drag the polymer particles and to facilitate their flow through the restriction, it may be advantageous to introduce a gas stream, hereinafter referred to as "dosing gas". Preferably, said dosing gas is taken from the recycling line of unreacted monomers. The flow of polymer particles through said second polymerization zone is thus adjusted by means of the mechanical valve and the dosing gas introduced at the bottom of said second polymerization zone and, in particular, at a point just above the restriction and the mechanical valve. The higher the flow rate of the dosing gas and the opening of the mechanical valve, the higher the velocity of the polymer particles.

Due to the importance of monitoring the polymer velocity in the second polymerization zone, it is important to arrange a control system working on said polymer velocity. In an embodiment, the control method of the present invention is a closed-loop control system, i.e. the controlled variable is measured and the result of said measurement is used to manipulate one or more process variables. In particular, the flow rate of the dosing gas and the opening of the mechanical valve (process variables) respond to the output values of the photometric instrument, so as to maintain the velocity of the polymer particles (controlled variable) in the second polymerization zone in a range comprised between 0.1 and 1 m/s, preferably 0.2 and 0.7 m/s. The photometric instrument measures on-line the velocity of the polymer particles and returns in real-time an output signal that is processed by an evaluation unit, for example a programmable logic controller or a personal computer. The measured velocity value is compared to the desired polymer particles velocity or set point. If a difference exists, the controller changes the opening of the mechanical valve and the flow rate of the dosing gas. More precisely, if the measured velocity is below the set point, the controller increases the opening of the mechanical valve and the flow rate of the dosing gas and vice-versa. A proportional-integral controller (PI) can be convenient for the purpose.

Other features of the present invention will be clear from reading the description hereafter given with reference to the accompanying drawings, which are given for illustrative purpose not limiting the scope of the invention.

BRIEF DESCRIPTION OF THE DRAWINGS

Referring to FIG. 1, the light source 1 is a continuous light source, i.e. a stabilized high-luminance white-light source, for example a xenon compact-arc lamp with elliptical reflector, or a halogen lamp with condenser or a stabilized LED.

Figure 1:
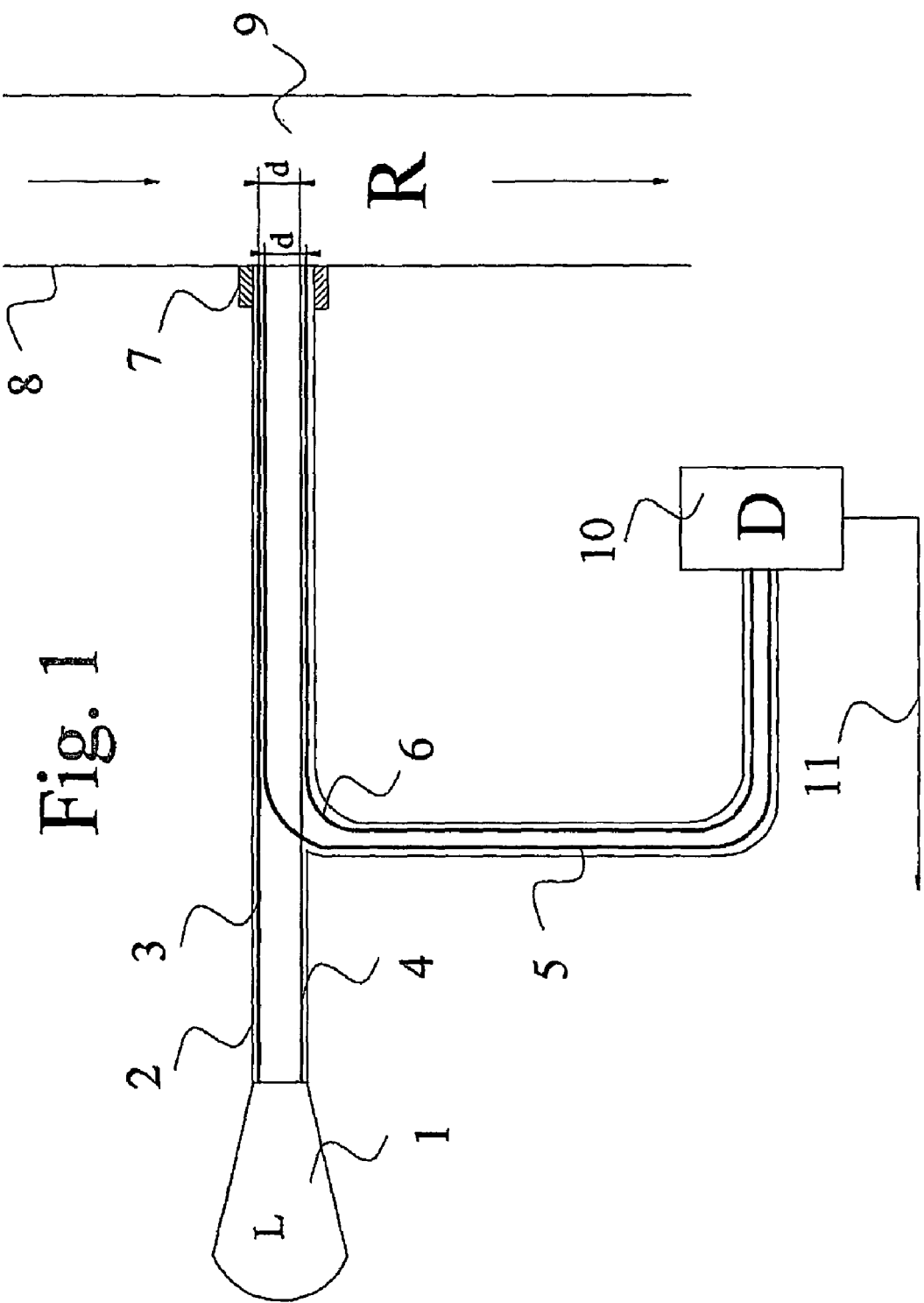
FIG. 1 is a diagrammatic representation showing a quasi-backscattering arrangement of the photometric instrument of the present invention applied to a polymerization reactor.

The bundle sheath 2, containing the transmitting optical waveguides 3 and 4 and the receiving optical waveguides 5 and 6, is screwed into the tap 7 made out in the wall 8 of the reactor 9.

When the light source 1 gives off a continuous light beam, the light travels along the transmitting optical waveguides 3 and 4 and strikes the polymer particles flowing downward in the reactor. The light scattered back by the polymer particles in the direction of incidence is received by the receiving optical waveguides 5 and 6, respectively, and sent to the evaluation unit 10. More precisely, the light transmitted by the transmitting optical waveguide 3 into the interior of the reactor is scattered back by the polymer particles and received by the receiving optical waveguide 5, that transmit it to the evaluation unit 10.

Analogously, the light transmitted by the transmitting optical waveguide 4 is received by the receiving optical waveguide 6.

The ends of the transmitting optical waveguides 3 and 4 and the receiving optical waveguides 5 and 6 are positioned flush with the wall of the reactor 9.

The evaluation unit 10 manages the whole system, from the transmission to the reception of the light signals. In particular, the light is converted into electrical signals and the electrical signals are converted in an output 11 indicative of the velocity of the polymer particles. In fact, by the comparison of the intensity between the two light signals carried by the receiving optical waveguides 5 and 6, that appear in a sinusoidal form, the evaluation unit can calculate a phase shift, which corresponds to the time it takes the polymer particles to cover the distance between the ends of said receiving optical waveguides 5 and 6. The velocity is then calculated by knowing the distance between the two corresponding receiving optical waveguides 5 and 6 along the flow of the polymer particles. Said distance d ranges between 0.2 and 6 mm.

Figure 2:
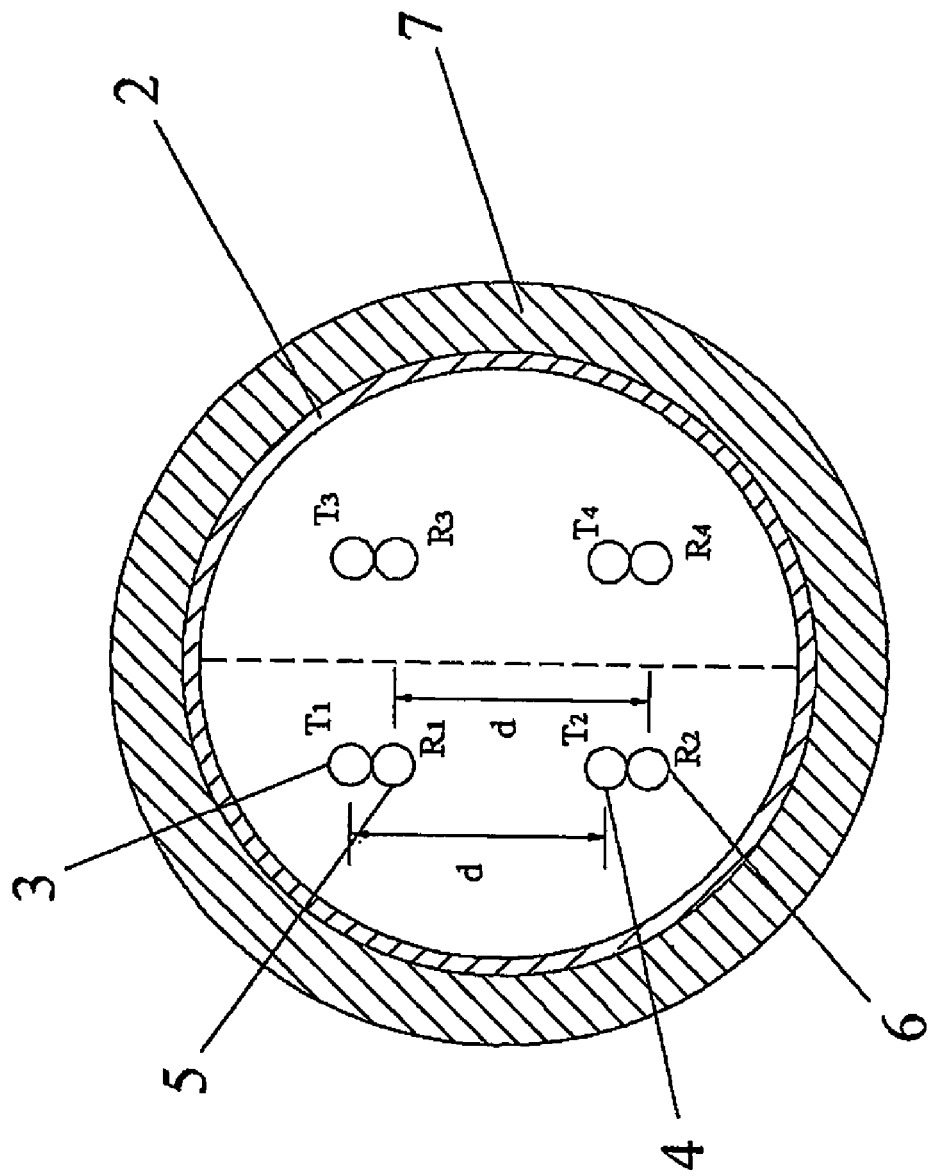
FIG. 2 is a diagrammatic representation of the reactor-side ends of the optical wave guides of the photometric instrument of FIG. 1 (front view).

Referring to FIG. 2, the front view of the reactor-side ends of the transmitting and receiving optical waveguides of the photometric instrument of FIG. 1 is given.

The reactor-side ends of the transmitting and receiving optical waveguides are arranged alongside one another in pairs. Four pairs of transmitting and receiving optical waveguides are provided, so that two independent velocity measurement are obtained: one from the couple $T_1/R_1-T_2/R_2$ and one from the couple $T_3/R_3-T_4/R_4$. In other words, the couple $T_3/R_3-T_4/R_4$ is the redundancy of the couple $T_1/R_1-T_2/R_2$.

The reactor-side ends $T_1$ and $T_2$ of the transmitting optical waveguides 3 and 4, that connect the interior of the reactor 9 to the light sources 1 of FIG. 1, are placed at the distance d above indicated. The same distance d separates the reactor-side ends $R_1$ and $R_2$ of the receiving optical waveguides 5 and 6 of FIG. 1.

Figure 3:
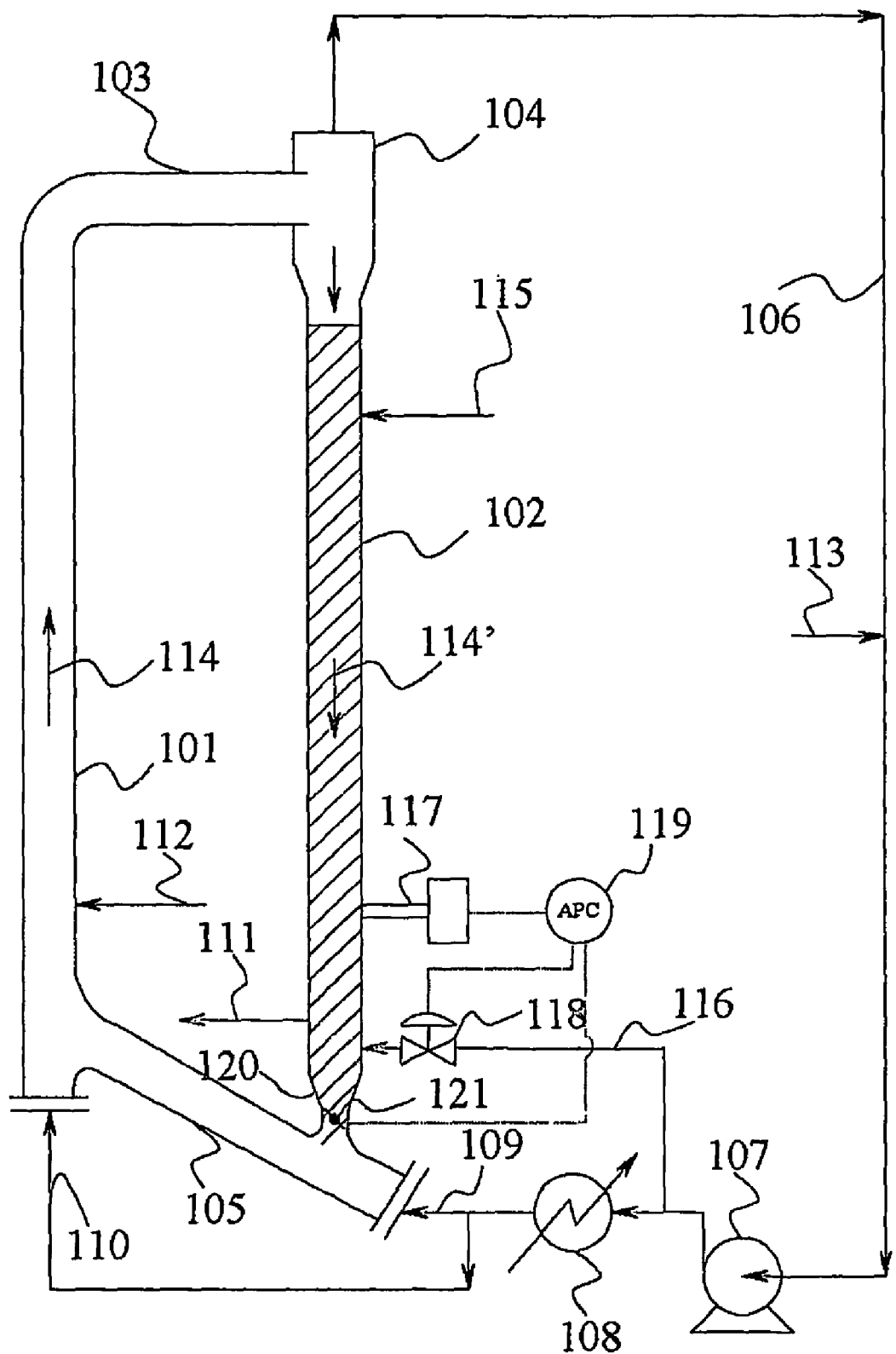
FIG. 3 is a diagrammatic representation of the control method of the present invention applied to the polymerization process described in EP 1 012 195.

Once a velocity measurement is obtained, it is possible to use it as a control variable in polymerization processes. In particular, referring to FIG. 3, the photometric instrument 117 is applied to the measurement of the polymer circulation rate in the gas phase process disclosed in EP 1 012 195.

The growing polymer flows through the first polymerization zone 101 under fast fluidization conditions along the direction of the arrow 114. In the second polymerization zone 102, the growing polymer flows in a densified form under the action of gravity along the direction of the arrow 114'. The two polymerization zones 101 and 102 are appropriately interconnected by the sections 103 and 105. The material balance is maintained by feeding in monomers and catalysts and discharging polymer.

Generally, the condition of fast fluidization in the first polymerization zone 101 is established by the gas mixture comprising one or more components coming from section 105, which is fed through a line 109, that permits also the transfer of the polymer from the second polymerization zone 102 to the first polymerization zone 101. Part of the gaseous mixture can be fed to the first polymerization zone 101 through a line 110 placed below the point of reintroduction of the polymer into said first polymerization zone 101.

The velocity of the transport gas injected into said first polymerization zone 101 has to be higher than the transport velocity under the operating conditions, and depends on the gas density and the particle size distribution of the solid. It is preferably comprised between 0.5 and 15 m/s, more preferably between 0.8 and 5 m/s.

The polymer and the gaseous mixture leaving said first polymerization zone 101 are conveyed to a solid/gas separation zone 104. The solid/gas separation can be effected by using conventional separation means such as, for example, a separator of the inertial type or of the centrifugal type, or a combination of the two.

From the separation zone 104, the polymer enters the second polymerization zone 102. The gaseous mixture leaving the separation zone 104 is compressed, cooled and transferred, if appropriate with addition of make-up monomers and/or molecular weight regulators and/or inert gases, to the first polymerization zone 101 through the line 109. The transfer of the gaseous mixture is effected by means of a recycle line 106, equipped with means for compression 107 and cooling 108 and a line 113 for feeding monomers, molecular weight regulators and, optionally, inert gases. A part of the gaseous mixture leaving the separation zone 104 can be transferred, after having been compressed and cooled, to the bottom of said first polymerization zone 101 through the line 110. Almost all the gas sent to said first polymerization zone 101 can be introduced through line 110, while a smaller amount needed to regulate the flow of polymer coming from the second polymerization zone 102 and to transport it through section 105 can be introduced through the line 109.

Generally, the various catalyst components are fed to the first polymerization zone 101 through a line 112 that is preferably placed in the lower part of the first polymerization zone 101. The polymer can be discharged through a line 111 advantageously placed in the second polymerization zone 102, where the polymer particles flow in a more packed form, so to minimize the quantity of entrained gas.

The gas mixture that is separated from the circulating solid in the separation zone 104 can be prevented to enter the second polymerization zone 102. This can be achieved by feeding a gas and/or liquid into the second polymerization zone 102 through a line 115 placed at a suitable point of said second polymerization zone 102, preferably in the upper part thereof. The gas and/or liquid mixture to be fed into the second polymerization zone 102 should have an appropriate composition, different from that of the gas mixture present in the first polymerization zone 101. Said gas and/or liquid mixture partially or totally replaces the gas mixture entrained with the polymer particles entering the downcorner. The flow rate of this gas feed can be regulated so that a flow of gas counter-current to the flow of polymer particles is originated in the second polymerization zone 102, particularly at the top thereof, thus acting as a barrier to the gas mixture coming from the first polymerization zone 101 which is entrained among the polymer particles.

A restriction 120 shaped like a funnel can be conveniently shaped at the bottom of said second polymerization zone 102 and a mechanical valve 121 is placed therein.

As previously explained, the flow of polymer particles through the bottom of said second polymerization zone 102 is conveniently adjusted by changing the opening of the mechanical valve 121 and the flow rate of the dosing gas. Said dosing gas is fed into the lower part of the second polymerization zone by means of a line 116 placed just above the restriction 120. The gas to be introduced through line 116 is conveniently taken from the recycle line 106, more precisely, upstream the cooling means 108. The flow rate of the dosing gas is adjusted by means of a pneumatic control valve 118, placed on the line 116, which is for instance a mechanical valve, such as a butterfly valve.

The photometric instrument 117 is preferably placed above said line 116 and fitted to the wall of the second polymerization zone 102. As a consequence, the photometric instrument 117 provides an evaluation of the velocity of the polymer particles flowing in said second polymerization zone 102, the evaluation being converted into a digital signal which is sent to an Advanced Process Controller (APC) 119.

Depending on the evaluation of the velocity, the APC 119 acts on the opening of the valve 118 so adjusting the flow rate of the dosing gas introduced into the second polymerization zone 102. Furthermore, the ACP 119 is also capable of adjusting the opening of the mechanical valve 121. As a result, the APC 119 controls the velocity of the polymer particles maintaining said velocity at the desired value.

The invention claimed is:

1. A method for monitoring the velocity of growing polymer particles, the method comprising:
    measuring by means of a photometric instrument a degree of attenuation in the propagation of light in a two-phase stream flowing in a polymerization reactor, the photometric instrument comprising:
    at least two transmitting optical waveguides connecting at least one light source to said two-phase stream; and
    at least two receiving optical waveguides connecting said two-phase stream to a light detector, the at least two transmitting optical waveguides and the at least two receiving optical waveguides having reactor-side ends,
    the polymerization reactor comprising a wall, wherein the reactor-side ends of said transmitting and said receiving optical waveguides are positioned flush with respect to the wall of said reactor,
    wherein the two-phase stream is a gas/solid or liquid/solid stream, the solid in the solid/gas or solid/liquid two-phase stream comprises polymer particles, and the reactor-side ends of the transmitting and receiving optical waveguides are arranged alongside one another in at least one pair, and
    wherein the velocity of the growing polymer particles is monitored in a polymerization process and is calculated from the time it takes to cover the distance between the reactor-side ends of the receiving optical waveguides.

2. The method according to claim 1, wherein said two-phase stream is a gas/solid stream.

3. The method according to claim 1, wherein said two-phase stream is a liquid/solid stream.

4. The method according to claim 1, wherein a polymer concentration, measured as volume of polymer per volume of reactor, in said two-phase stream is comprised between 5 and 70%.

5. The method according to claim 1, wherein the flow of polymer particles is substantially along one direction.

6. The method according to claim 1, wherein said transmitting and receiving optical waveguides are arranged in a quasi-backscattering arrangement on the wall of a polymerization reactor.

7. The method according to claim 1 wherein the distance between the reactor-side ends of said two receiving optical waveguides is less than 10 mm.

8. The method according to claim 7 wherein said distance is 0.2 to 6 mm.

9. The method for monitoring the velocity of polymer particles according to claim 1, wherein the polymerization process comprises polymerizing at least one α-olefin in a gas-phase process in which the growing polymer particles flow upward through a first polymerization zone under fast fluidization conditions, leave said first polymerization zone and enter a second polymerization zone comprising a bottom through which they flow in a densified form under the action of gravity, leave said second polymerization zone and are reintroduced into said first polymerization zone, thus establishing a circulation of polymer between the two polymerization zones.

10. The method according to claim 9, wherein the photometric instrument is arranged on the bottom part of said second polymerization zone.

11. The method according to claim 9, wherein in said second polymerization zone a polymer concentration, measured as volume of polymer per volume of reactor, is comprised between 30 and 60%.

12. The method according to claim 9, wherein in said second polymerization zone a temperature is between 50° C. and 120° C.

13. The method according to claim 9, wherein in said second polymerization a pressure is between 1.5 MPa and 6 MPa.

14. The method according to claim 9, further comprising adjusting the flow of polymer particles by introducing dosing gas at a gas flowrate into the bottom of said second polymerization zone.

15. The method according to claim 14, wherein the flow rate of said dosing gas responds to an output value of said photometric instrument so as to maintain the velocity of the polymer particles in a range comprised between 0.1 and 1 m/s.

16. The method according to claim 9, wherein the flow of polymer particles through said second polymerization zone is adjusted by means of an opening of a mechanical valve placed at the bottom of said second polymerization zone.

17. The method according to claim 16, wherein the opening of said mechanical valve responds to an output value of said photometric instrument so as to maintain the velocity of the polymer particles in a range comprised between 0.1 and 1 m/s.

18. The method according to claim 16, wherein said mechanical valve is a butterfly valve.

19. A method for monitoring the velocity of growing polymer particles in an α-olefin polymerization process, the method comprising:
    measuring by means of a photometric instrument a degree of attenuation in the propagation of light in a two-phase stream flowing in a polymerization reactor, the photometric instrument comprising:
    at least two transmitting optical waveguides connecting at least one light source to said two-phase stream; and
    at least two receiving optical waveguides connecting said two-phase stream to a light detector, the at least two transmitting optical waveguides and the at least two receiving optical waveguides having reactor-side ends,
    the polymerization reactor comprising a wall, wherein the reactor-side ends of said transmitting and said receiving optical waveguides are positioned flush with respect to the wall of said reactor, wherein the two-phase stream is a gas/solid or liquid/solid stream, the solid in the solid/gas or solid/liquid two-phase stream comprises polymer particles of α-olefins, and the particles flow uniformly through the polymerization reactor at a rate between 0.1 and 1 m/s in substantially one direction, relative motion between adjacent particles is virtually absent and the reactor-side ends of the transmitting and receiving optical waveguides are arranged alongside one another in at least one pair, and wherein the velocity of the polymer particles of α-olefins is calculated from the time it takes to cover the distance between the reactor-side ends of the receiving optical waveguides.

* * * * *